US011796468B2

(12) United States Patent
Mano (10) Patent No.: US 11,796,468 B2
(45) Date of Patent: Oct. 24, 2023

(54) GAS MEASUREMENT DEVICE AND GAS MEASUREMENT METHOD

(71) Applicant: Shimadzu Corporation, Kyoto (JP)

(72) Inventor: Kazune Mano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 459 days.

(21) Appl. No.: 17/277,243

(22) PCT Filed: Aug. 29, 2019

(86) PCT No.: PCT/JP2019/033844
§ 371 (c)(1),
(2) Date: Mar. 17, 2021

(87) PCT Pub. No.: WO2020/059452
PCT Pub. Date: Mar. 26, 2020

(65) Prior Publication Data
US 2021/0262929 A1    Aug. 26, 2021

(30) Foreign Application Priority Data
Sep. 20, 2018 (JP) .................. 2018-175946

(51) Int. Cl.
*G01N 21/39* (2006.01)
*G01J 3/42* (2006.01)
(Continued)

(52) U.S. Cl.
CPC ............. *G01N 21/39* (2013.01); *G01J 3/42* (2013.01); *G01N 1/2273* (2013.01); *G01N 33/0006* (2013.01); *G01J 2003/423* (2013.01)

(58) Field of Classification Search
CPC .. G01N 21/39; G01N 1/2273; G01N 33/0006; G01J 3/42; G01J 2003/423; G01J 3/28
See application file for complete search history.

(56) References Cited

U.S. PATENT DOCUMENTS 7,259,856 B2 *  8/2007  Kachanov ............. G01N 21/39
                                              356/437
9,285,306 B2 *  3/2016  MacGregor ........ G01N 21/3504
(Continued)

FOREIGN PATENT DOCUMENTS

JP    2006-234810 A    9/2006
JP    2011-119541 A    6/2011
(Continued)

OTHER PUBLICATIONS

Written Opinion for PCT application No. PCT/JP2019/033844 dated Nov. 12, 2019, submitted with a machine translation.
(Continued)

*Primary Examiner* — Freddie Kirkland, III
(74) *Attorney, Agent, or Firm* — Muir Patent Law, PLLC (57) ABSTRACT

According to an aspect of the present invention, a gas measurement apparatus includes a measurement controller (6), a spectrum generator (72), a processing unit (73), and a result obtaining unit (74). The measurement controller (6) controls the apparatus so that a laser-light source (1) causes laser light to be incident to an optical resonator (4) and a wavelength of the laser light is scanned within a predetermined wavelength range, the range including an absorption peak of a target component, thereby performing a CRDS measurement. The spectrum generator (72) generates an absorption spectrum based on data obtained at each wavelength within a predetermined wavelength range. The processing unit (73) approximates a waveform shape of the absorption peak of the target component in the absorption spectrum with a polynomial and acquires a coefficient of a term of a predetermined degree in the polynomial. The result obtaining unit (74) obtains absorption intensity from the coefficient, based on predetermined reference information indicating a correspondence relation between a coefficient of (Continued)

the term of the predetermined degree and the absorption intensity.

8 Claims, 5 Drawing Sheets

(51) Int. Cl.
*G01N 1/22* (2006.01)
*G01N 33/00* (2006.01)

(56) References Cited

U.S. PATENT DOCUMENTS

| | | | |
|---|---|---|---|
| 9,772,277 B2* | 9/2017 | Muramatsu | G01N 21/3103 |
| 9,778,110 B1* | 10/2017 | Rella | G01J 3/10 |
| 10,928,313 B2* | 2/2021 | Koulikov | G01N 21/31 |
| 11,209,356 B2* | 12/2021 | Mano | G01N 21/39 |
| 2006/0181710 A1 | 8/2006 | Kachanov et al. | |
| 2010/0296095 A1* | 11/2010 | Hong | G01N 21/534 |
| | | | 356/436 |
| 2013/0144561 A1* | 6/2013 | Harb | G01N 21/31 |
| | | | 702/189 |
| 2015/0338342 A1 | 11/2015 | Muramatsu et al. | |
| 2018/0011011 A1* | 1/2018 | Foldes | G01N 21/3504 |
| 2018/0156718 A1* | 6/2018 | Fleisher | G01J 3/0208 |

FOREIGN PATENT DOCUMENTS

| | | |
|---|---|---|
| WO | 2014/106940 A1 | 10/2014 |
| WO | 2014/170828 A1 | 10/2014 |

OTHER PUBLICATIONS

Koji Hashiguchi, "A survey on high-efficiency measurement techniques of trace moisture in gases", AIST Bulletin of Metrology vol. 9, No. 2, pp. 185-205, Oct. 2015, submitted with a machine translation.

Terabayashi et al., "Development of Analytical Method for 14C Determination in Biomedical Sample by Laser Spectroscopy", Radioisotopes, 67, pp. 85-91, 2018 (including English Abstract), submitted with a machine translation.

Abe et al., "Performance evaluation of a trace-moisture analyzer based on cavity ring-down spectroscopy: Direct comparison with the NMIJ trace-moisture standard", Sensors and Actuators A, 165, pp. 230-238, 2011.

* cited by examiner

Fig. 3A (A) CRD SIGNAL

Fig. 3B (B) 2F SIGNAL (= B2)

GAS MEASUREMENT DEVICE AND GAS MEASUREMENT METHOD

TECHNICAL FIELD

The present invention relates to a gas measurement apparatus and a gas measurement method for measuring the concentration of a specific component in a measured gas by using absorption of laser light, and more specifically, a gas measurement apparatus and a gas measurement method using cavity ring-down absorption spectroscopy.

BACKGROUND ART

Laser absorption spectroscopy is widely used as a method for measuring the concentration of a specific component in a measured gas. Laser absorption spectroscopy includes direct laser absorption spectroscopy, laser-wavelength-modulation absorption spectroscopy, cavity ring-down absorption spectroscopy, and the like (see Patent Literature 1 and the like).

In direct laser absorption spectroscopy and laser-wavelength-modulation absorption spectroscopy, generally, laser light is cast into a measurement cell containing a measured gas, and a photodetector detects the intensity of the light obtained by being absorbed by a gas component in the process of passing through the measurement cell. The long effective optical path length for light absorption is desired to improve the detection sensitivity, but, in such laser absorption spectroscopy, the effective optical path length mainly depends on the size of the measurement cell. On the other hand, in cavity ring-down absorption spectroscopy (referred to as "CRDS" below according to conventional practice), it is possible to greatly improve the detection sensitivity by lengthening the effective optical path length for light absorption using an optical resonator (see Non Patent Literature 1 and the like).

Figure 4:
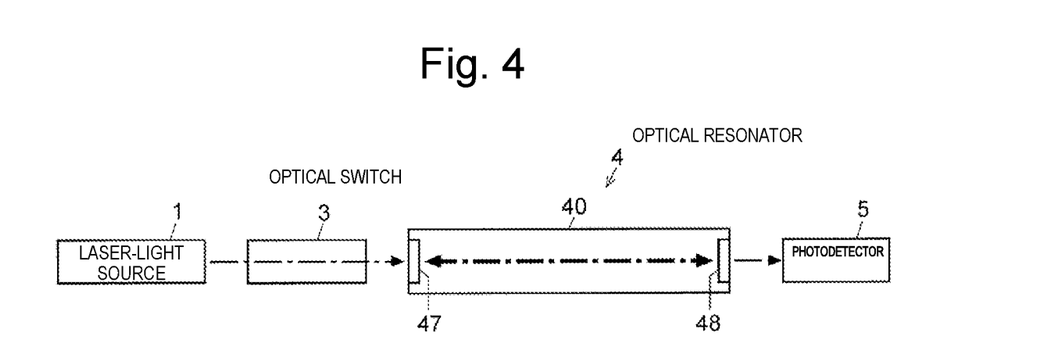
FIG. 4 is a schematic configuration diagram of a general CRDS apparatus.

The basic measurement principle in a CRDS apparatus will be described. FIG. 4 is a schematic configuration diagram centering on an optical path in a general CRDS apparatus.

In FIG. 4, laser light of a predetermined wavelength, which is emitted from a laser-light source 1 passes through an optical switch 3 and then is introduced into a measurement cell 40 containing a measured gas. A pair of high-reflectance (very slightly light-transmitting) mirrors 47 and 48 are arranged at both ends of the tubular measurement cell 40 to face each other. The measurement cell 40 and the mirrors 47 and 48 constitutes an optical resonator 4. The optical resonator 4 is a Fabry-Perot resonator similar to that generally used in, for example, a laser device. The wavelength (frequency) of light that may resonate is determined in accordance with a resonance condition. Note that, the optical resonator 4 may be a ring-like resonator configured by three or more mirrors, instead of the resonator having a configuration in which two mirrors are arranged to face each other.

Figure 5:
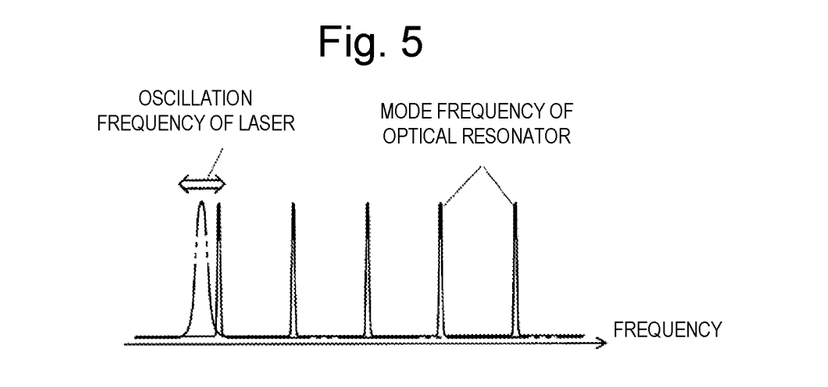
FIG. 5 is a schematic diagram illustrating a relation between a mode frequency of an optical resonator and an oscillation frequency of laser light.

The frequency that may resonate in the optical resonator 4 is generally referred to as a mode frequency. As illustrated in FIG. 5, the mode frequency is provided at predetermined frequency intervals. When the frequency of the laser light introduced into the optical resonator 4 does not coincide with the mode frequency, the power of the light is not accumulated in the optical resonator 4. On the other hand, when the oscillation frequency of the laser light in the laser-light source 1 is adjusted to coincide with the mode frequency, the power of the light is accumulated in the optical resonator 4.

In the CRDS apparatus, after the power of light is sufficiently accumulated in the optical resonator 4, the laser light incident to the optical resonator 4 is instantaneously blocked by the optical switch 3. The light thus accumulated in the optical resonator 4 then reciprocates many times (actually several thousand to tens of thousands times) between the pair of mirrors 47 and 48. During this time, the light is gradually absorbed by a component of a measured gas contained in the measurement cell 40 and becomes attenuated. During this process, the photodetector 5 repeatedly detects a portion of the attenuating light leaking outside through one of the mirrors 48 of the optical resonator 4. By obtaining the time constant (ring-down time) of light attenuation based on data detected by this photodetector 5, it is possible to calculate the absorption coefficient of a target component in the measured gas at the frequency of the laser light at this time. Then, it is possible to obtain the absolute concentration of the target component from the absorption coefficient. Further, by repeating similar measurements while scanning the oscillation frequency of the laser light in the laser-light source 1, it is possible to obtain the absorption spectrum of the target component in the measured gas.

The following equation (1) is usually used to obtain the absorption coefficient $\alpha$ of the target component in the measured gas (see Patent Literature 2 and the like).

$$\alpha = 1/c\{(1/\tau) - (1/\tau_0)\} \quad (1)$$

Here, c is the velocity of light, $\tau$ is the ring-down time when the measured gas is contained in the measurement cell 40, and $\tau_0$ is the ring-down time in a reference state when the measured gas is not contained in the measurement cell 40 (for example, in a vacuum state) or when the absorption by the component in the measured gas can be completely negligible. Further, the relation between the absorption coefficient $\alpha$ of the target component (absorbent substance), the number density n of the target component molecules per unit volume, and the absorption cross-sectional area 6 by the target component is as shown in the following equation (2).

$$\alpha = n\sigma \quad (2)$$

Thus, using equations (1) and (2), it is possible to calculate the absolute concentration of the component of which the absorption cross-sectional area is known, from the ring-down times $\tau$ and $\tau_0$. In the CRDS apparatus, the distance through which light passes in the measured gas is extended by using the optical resonator 4, so that the difference between the ring-down times $\tau$ and $\tau_0$ increases. Thus, it is possible to detect even a very small amount of light absorption due to a trace amount of the target component, and to realize higher detection sensitivity as compared with other methods of laser absorption spectroscopy.

CITATION LIST

Patent Literature

Patent Literature 1: WO 2014/106940 A
Patent Literature 2: JP 2011-119541 A

Non Patent Literature

Non Patent Literature 1: Koji HASHIGUCHI, "A survey on high-efficiency measurement techniques of trace moisture in gases", AIST Bulletin of Metrology Vol. 9, No. 2, pp. 185-205, October 2015

SUMMARY OF INVENTION

Technical Problem

As described above, in the CRDS apparatus, it is possible to obtain the absorption coefficient of the concentration in the measured gas with very high sensitivity, and it is often used for ultrasensitive measurement of the gas concentration. When the gas concentration is calculated quantitatively, the height from the baseline to the top of an absorption peak in the absorption spectrum is required. However, in the CRDS apparatus, the measured value may drift depending on the state of the device, which may cause the ring-down time to change slightly each time the ring-down time is measured. There are mainly the following factors in the drift of the measured value.

(1) Decrease in the effective reflectance of the mirrors 47 and 48 constituting the optical resonator 4 due to the adhesion of substances in the measured gas to the mirrors 47 and 48.

(2) Changes in the effective reflectance of the mirrors 47 and 48 due to minute shift in the mirrors 47 and 48 and minute change in the position of the incident light on the mirrors 47 and 48, and effective change in the optical resonator length (that is, an optical path length).

(3) Change in the optical resonator length due to thermal expansion or contraction caused by changes in ambient temperature.

Figure 6:
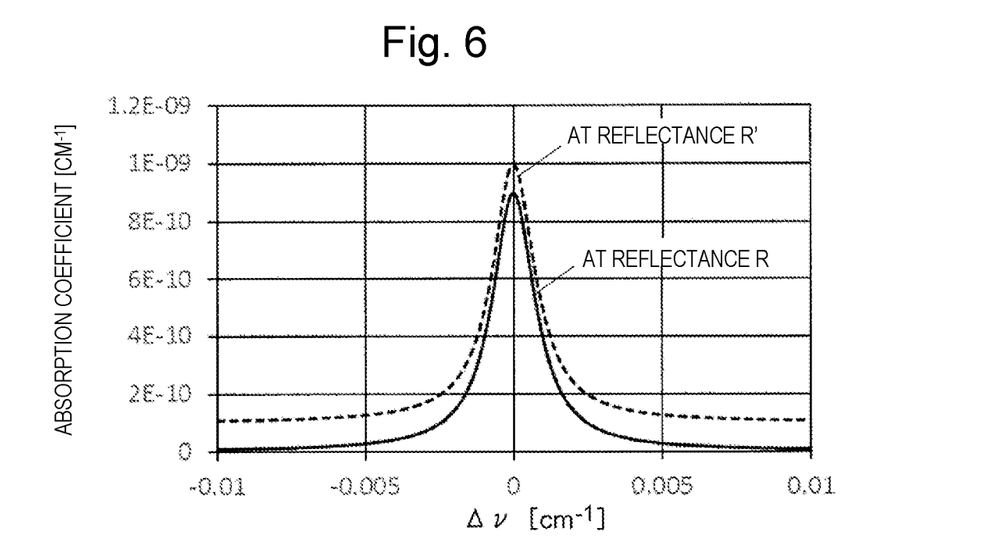
FIG. 6 is a diagram illustrating an example of a change in an absorption spectrum when the effective reflectance of a mirror in the optical resonator decreases during a period from when the ring-down time $\tau_0$ is measured until the ring-down time $\tau$ is measured.

FIG. 6 is a diagram illustrating an example of a change in the absorption spectrum when the effective reflectance of the mirrors 47 and 48 of the optical resonator 4 decreases from R to R', due to the above factors, during a period from when the ring-down time $\tau_0$ is measured until the time when the ring-down time $\tau$ is measured. As described above, when the reflectance decreases, an absorption peak is shifted in a direction in which the absorption coefficient increases (upward in FIG. 6). Therefore, it is not possible to accurately calculate the component concentration simply by obtaining the value of the absorption coefficient at the position (wavenumber) of the absorption peak, and it is necessary to acquire the value of the height from the baseline to the peak top at the position of the absorption peak and calculate the absorption coefficient.

In particular, in isotope ratio measurement for a sample derived from a living body, samples are repeatedly collected for a long period of several weeks or longer, and the change in the isotope ratio contained in the samples for the long period of time is measured. Therefore, there is a possibility that the influence of the drift of the measured value as described above becomes more remarkable.

In order to reduce the influence of the drift of the measured value, a method of measuring a standard gas, of which component concentration is controlled, periodically or immediately before or after the measurement of the measured gas, and performing calibration based on the measurement result of the standard gas is generally adopted. However, it is necessary to measure the standard gas in addition to the measured gas, and there is a problem that the measurement throughput is lowered. Further, another problem is that it is not possible to cope with the drift occurring in a relatively short time, such as the drift occurring between the measurement time of the measured gas and the measurement time of the standard gas.

The present invention has been made in view of the above problems, and an object of the present invention is to provide a gas measurement apparatus and a gas measurement method capable of reducing the influence of the drift of the measured value including fluctuation that occur in a relatively short time and calculating the concentration of a target component with high accuracy, without decreasing the measurement throughput, in the gas measurement apparatus using the CRDS.

Solution to Problem

The applicant has proposed in Patent Literature 1 a method of obtaining a curve corresponding to a profile of the harmonic signal of a modulation frequency in laser-wavelength-modulation absorption spectroscopy and calculating the concentration, the pressure, the temperature, and the like of a measured gas from the obtained curve, by performing mathematical arithmetic processing on the absorption spectrum obtained by performing measurement while scanning with the wavelength of laser light in the direct laser absorption spectroscopy. The purpose of this method is to obtain highly-accurate measurement results close to the results of laser-wavelength-modulation absorption spectroscopy that modulates the wavelength of laser light, from the measurement results of direct laser absorption spectroscopy that does not modulate the wavelength of the laser light. It is possible to perform robust gas measurement that does not depend on the light intensity, by performing normalization processing in consideration of changes in the intensity of the laser light casted into the measured gas.

On the other hand, in the CRDS, although the measurement accuracy does not depend on the intensity of the laser light cast into the measured gas due to the measurement principle, factors such as a decrease in the reflectance of the mirror constituting the optical resonator cause the drift of the measured value, as described above. Although it is not assumed in the CRDS that measurement by modulating the wavelength of the laser light is actually performed, the present inventor has come up with the idea of applying the method disclosed in Patent Literature 1 to the CRDS in order to reduce the influence of the drift of the measured values due to the above factors, and the inventor has verified the effectiveness of the present invention, examined the processing contents when applied to the CRDS and the optimization of the procedure, and completed the present invention.

That is, according to an aspect of the present invention, which has been made to solve the above problems, a gas measurement apparatus for obtaining concentration of a target component in a gas to be measured by cavity ring-down absorption spectroscopy includes a laser-light source configured to have a variable wavelength, an optical resonator which includes a pair of highly-reflective mirrors and a measurement cell in which the gas to be measured is to be contained, and resonates laser light which is emitted from the laser-light source and is introduced into the measurement cell, and an optical detection unit configured to detect laser light output from the optical resonator. The gas measurement apparatus includes: a measurement controller configured to control the apparatus so that the laser-light source causes laser light to be incident to the optical resonator, and a wavelength of the laser light is scanned within a predetermined wavelength range, the range including an absorption peak of the target component, thereby performing the cavity ring-down absorption spectroscopy measurement through an output of the optical detection unit while; a spectrum generator configured to generate an absorption spectrum based on data obtained at each wavelength within the predetermined wavelength range under the control of the measurement controller; a processing unit configured to approximate a waveform shape of the absorption peak of the target component in the absorption spectrum with a polynomial and configured to acquire a coefficient of a term of a predetermined degree in the polynomial; and a result obtaining unit configured to obtain absorption intensity from the coefficient obtained by the processing unit based on predetermined reference information indicating a correspondence relation between a coefficient of the term of the predetermined degree and the absorption intensity.

Further, according to another aspect of the present invention which has been made to solve the above problems, a gas measurement method is for obtaining concentration of a target component in a gas to be measured by cavity ring-down absorption spectroscopy. The gas measurement method includes: a measurement step of performing the cavity ring-down absorption spectroscopy measurement through optical detection while laser light is incident to an optical resonator and a wavelength of the laser light is scanned within a predetermined wavelength range including an absorption peak of the target component, the optical resonator including a pair of high-reflective mirrors and a measurement cell in which the gas to be measured is contained; a spectrum generation step of generating an absorption spectrum based on data obtained at each wavelength within the predetermined wavelength range in the measurement step; a processing step of approximating a waveform shape of the absorption peak of the target component in the absorption spectrum with a polynomial and acquiring a coefficient of a term of a predetermined degree in the polynomial; and a result obtaining step of obtaining absorption intensity from the coefficient based on predetermined reference information indicating a correspondence relation between a coefficient of the term of the predetermined degree and the absorption intensity.

In the gas measurement apparatus in the above aspect of the present invention, the measurement controller controls units such as the laser-light source to measure a gas to be measured (measured gas) at each wavelength within a predetermined wavelength range with a CRDS. The spectrum generator obtains a ring-down time based on the data obtained by the measurement at each different wavelength, and calculates the absorption coefficient based on a ring-down time measured in this measurement and a ring-down time in a reference state acquired in advance. Then, the absorption spectrum indicating a change in the absorption coefficient within a predetermined wavelength range including the wavelength of the absorption peak of the target component is generated from the absorption coefficient of each wavelength.

Note that, since the wavelength is the reciprocal of the wavenumber, it is natural that the "wavelength" here can be replaced with the "wavenumber". Here, a wavelength scanning range may be set to a predetermined range centering on the known absorption wavelength of the target component being a target for obtaining the concentration, and the predetermined range may be set to a value determined in accordance with the width of the assumed absorption peak.

The processing unit approximates the waveform shape within the predetermined wavelength range including the peak top of the absorption peak of the target component in the obtained absorption spectrum with a polynomial of a predetermined degree. Typically, a fitting processing is performed in which the waveform shape of the absorption peak is, or the values of the absorption coefficients obtained as a result of measurement at each wavelength are, approximated with a polynomial of the second order or higher. In the method disclosed in Patent Literature 1, a polynomial approximation is performed in each range of a predetermined wavelength width at each point of the wavelength over a wide wavelength range including the entirety of the absorption peak, in order to generate a curve corresponding to a profile of a harmonic signal (2f signal, 1f signal) of a modulation frequency in laser-wavelength-modulation absorption spectroscopy, based on the absorption spectrum obtained by direct laser absorption spectroscopy. On the other hand, in the present invention, since it is only necessary to be able to approximate the waveform within a predetermined wavelength range including the peak top of the absorption peak, the polynomial approximation may be performed only on one wavelength range in the vicinity of the peak top of the absorption peak.

Note that, in the fitting processing, for example, various known methods such as the least square method can be used. In addition, although it is usually sufficient to use a quadratic polynomial as the polynomial, a higher-order polynomial may be used.

When the measured value drifts by factors such as a change in reflectance of the mirror and a change in an optical resonator length as described above, the absorption spectrum changes as illustrated in FIG. 6. However, the change is mainly a shift of the baseline in the background, and there is almost no change in the waveform shape itself of the absorption peak by the target component. Therefore, as described above, there is almost no or little effect of the above drift on the value of the coefficients of the second-order or even-order terms of the approximate polynomial obtained by fitting to the waveform of the absorption peak, which is the actual measurement result. Further, as described above, since the measured value of the ring-down time in the CRDS does not depend on the intensity of the laser light, the coefficient of each term of the approximate polynomial is not influenced by the fluctuation or difference in the intensity of the laser light, and normalization processing as performed by the method disclosed in Patent Literature 1 is not necessary. Thus, the coefficients of the even-order terms of the approximate polynomial reflect the absorption coefficient of the target component excluding the influence of the drift of the measured value. Therefore, the processing unit acquires a coefficient of a predetermined degree in the approximate polynomial, for example, a quadratic term.

When the temperature and pressure of the measured gas are constant, that is, under the same conditions, it is considered that the coefficient of the term of the predetermined degree depends on the type of the target component and the concentration of the target component, and does not depend on the drift of the measured value and the like. Therefore, for the target component, reference information indicating a correspondence relation between the coefficient and the absorption intensity is predetermined based on the experimental results and the like, and is stored in a memory, for example. The result obtaining unit uses the reference information to obtain the absorption intensity from the coefficient obtained by the processing unit. Here, the absorption intensity may be either an absorption coefficient or an absolute concentration obtained from the absorption coefficient and the absorption cross-sectional area. That is, the result obtaining unit can obtain the absorption coefficient and the absolute concentration immediately from the coefficient value using the reference information as a lookup table.

As described above, in the present invention, the polynomial may be a quadratic polynomial, and the term of the predetermined degree may be a quadratic term.

In this case, the measurement controller may perform wavelength scanning in a wavelength range necessary and sufficient for calculating the coefficient of the quadratic term of the polynomial.

In the method disclosed in Patent Literature 1, it is necessary to include the entirety of the absorption peak and to obtain the absorption spectrum over a wide wavelength range outside the absorption peak by measurement. On the other hand, in the present invention, as described above, it is only necessary to be able to approximate the waveform in the vicinity of the peak top of the absorption peak well. Thus, in general, the necessary and sufficient wavelength range may be set to a wavelength range corresponding to about ½ of a peak width centering on the wavelength of the absorption peak of the target component.

Accordingly, in the present invention, the number of wavelength points that need to be measured can be considerably reduced as compared with a case where the measurement is performed so as to cover the entirety of the absorption peak, for example. Thus, it is possible to achieve reduction in time required for measurement and improvement of the measurement throughput.

Advantageous Effects of Invention

According to the present invention, since it is not necessary to measure the standard gas in addition to the measured gas, it is possible to avoid a decrease in the measurement throughput even when the influence of the drift of the measured value is reduced. Further, since it is possible to remove not only the drift of the measured value for a long time but also the influence of the fluctuation of the measured value in a relatively short time with high accuracy, it is possible to calculate the concentration of the target component with high accuracy.

DESCRIPTION OF EMBODIMENTS

Figure 1:
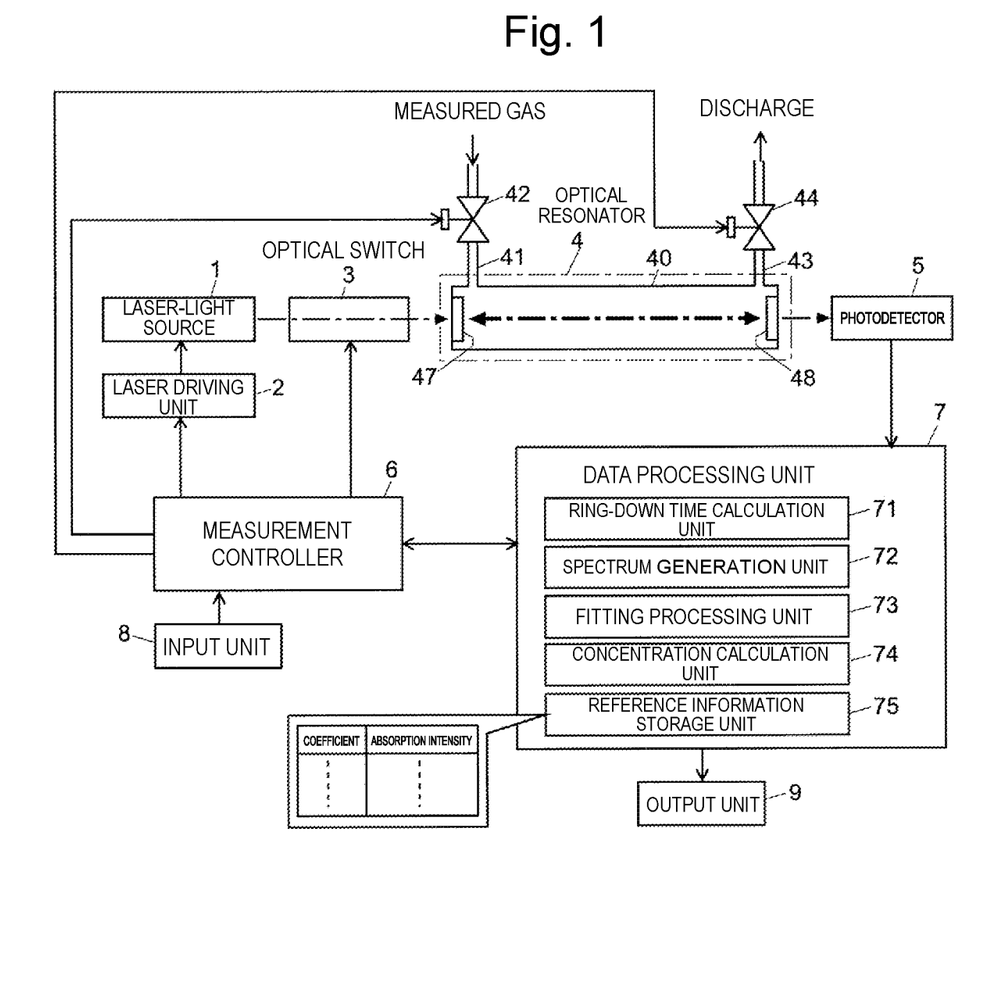
FIG. 1 is a configuration diagram of a main part of a CRDS apparatus according to an embodiment of the present invention.

Hereinafter, a gas measurement apparatus and a gas measurement method according to an embodiment of the present invention will be described with reference to the accompanying drawings. FIG. 1 is a schematic configuration diagram of the gas measurement apparatus in the present embodiment.

In the gas measurement apparatus in the present embodiment, the configuration of a measurement system is the same as the configuration of a general CRDS apparatus illustrated in FIG. 4. The gas measurement apparatus includes a laser-light source 1, a laser driving unit 2, an optical switch 3, an optical resonator 4, and a photodetector 5. The optical resonator 4 includes a substantially cylindrical measurement cell 40 that contains a sample gas being a measured gas, and a pair of high-reflectance mirrors 47 and 48 arranged at both ends of the measurement cell 40 to face each other. A gas introduction tube 41 and a gas discharge tube 43 are connected to the measurement cell 40. An introduction valve 42 is provided in the gas introduction tube 41. A discharge valve 44 is provided in the gas discharge tube 43.

The measurement controller 6 to which an input unit 8 is connected controls the units such as the laser driving unit 2 in order to perform measurement and data processing described later. In a memory (not illustrated) in the measurement controller 6, information such as an absorption peak position (wavelength) and a wavelength scanning range corresponding to the type of the component to be measured is stored in advance. Further, the data processing unit 7 to which a detection signal by the photodetector 5 is input includes a ring-down time calculation unit 71, a spectrum generator 72, a fitting processing unit 73, a concentration calculation unit 74, a reference information storage unit 75, and the like as functional blocks. Further, an output unit 9 connected to the data processing unit 7 is, for example, a display monitor or the like.

Figure 2:
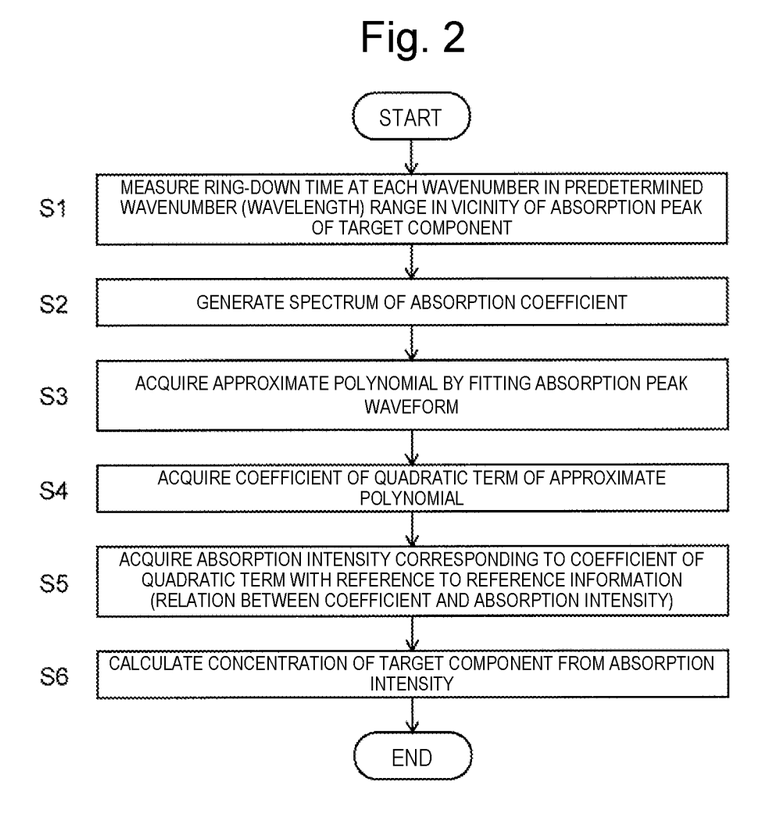
FIG. 2 is a flowchart illustrating an example of a procedure of measurement and processing when the concentration of a target component is obtained in the CRDS apparatus in the present embodiment.

A measurement operation and a processing operation when the concentration of the target component in the measured gas is obtained in the gas measurement apparatus in the present embodiment, that is, the gas measurement method performed by the present apparatus will be described with reference to FIGS. 1 and 2. FIG. 2 is a flowchart illustrating an example of a procedure of measurement and processing when the concentration of the target component is obtained using the gas measurement apparatus.

A user inputs the type of the target component and the like from the input unit 8 in advance.

The measurement controller 6 opens the introduction valve 42 in a state where the discharge valve 44 is closed, and introduces the measured gas into the measurement cell 40. When the pressure detected by a pressure sensor (not illustrated) reaches a predetermined value, the introduction valve 42 is closed and the measurement cell 40 is filled with the measured gas. Then, the measurement controller 6 acquires information on a wavelength range corresponding to the target component designated in advance, and performs measurement at each wavelength with the CRDS and measure a ring-down time while sequentially scanning the wavelength of laser light generated by the laser-light source 1 through the laser driving unit 2 within that wavelength range (Step S1: measurement step).

That is, at each wavelength within the predetermined wavelength range, the laser-light source 1 casts laser light into the measured gas in the measurement cell 40, and the optical switch 3 blocks the laser light at a predetermined timing. The ring-down time calculation unit 71 collects data detected by the photodetector 5 until a predetermined time elapses from immediately before the laser light is blocked. Then, the ring-down time $\tau$ is calculated for each wavelength based on the data.

Then, the spectrum generator 72 calculates the absorption coefficient at each wavelength, based on the ring-down time τ based on the actually-measured data and the ring-down time $\tau_0$ in a reference state, which is stored in the reference information storage unit 75. Such a method of calculating the absorption coefficient is the same as the method in the related art. For example, the above equations (1) and (2) may be used. Then, by collecting the values of the absorption coefficient calculated at each wavelength, the absorption spectrum within the predetermined wavelength range is obtained (Step S2: spectrum generation step).

The absorption spectrum obtained at this time may include the influence of drift of the measured value due to the various factors described above. Therefore, the accurate concentration is calculated by removing fluctuations in the measured value including such drift in the following procedure. Firstly, the principle of removing the influence of fluctuations in the measured value will be described.

A case where the reflectance of the mirror of the optical resonator 4 is different (that is, drifting occurs) between when the ring-down time $\tau_0$ in the reference state is measured and when the ring-down time τ is measured for the measured gas is assumed. When the reflectance of the mirror in measurement of the ring-down time $\tau_0$ is set as R and the reflectance of the mirror in measurement of the ring-down time τ is set as R', a CRD signal S(ν) calculated from the measurement result is an equation (3) as follows.

$$S(\nu)=(1/c)\{(1/\tau)-(1/\tau_0)\}=(1/c)\{(c[(1-R')+\alpha(\nu)L]/L)-(c[1-R]/L)\}=\alpha(\nu)+(R-R')/L \quad (3)$$

Here, α(ν) is the absorption coefficient when the reflectance of the mirror does not fluctuate.

Figure 3A:
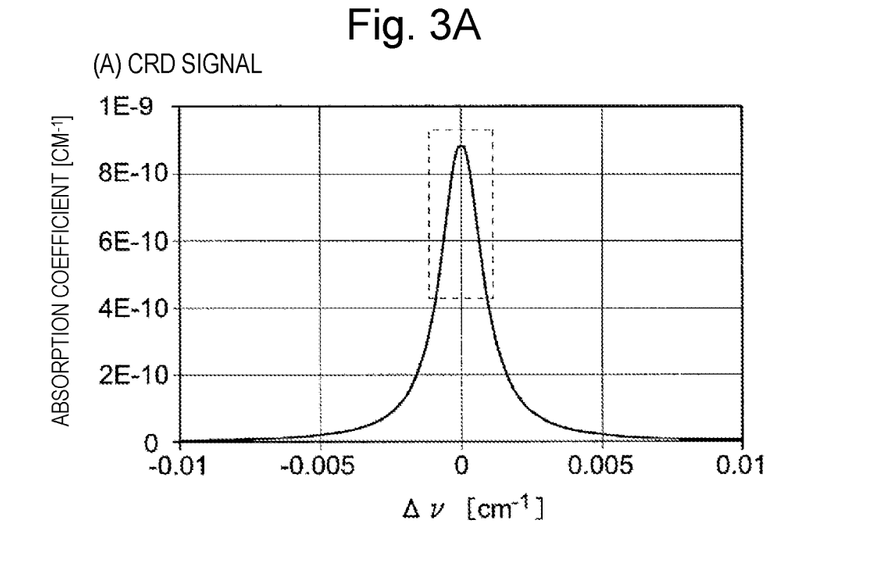
FIGS. 3A to 3D are diagrams for explaining the principle of a method for calculating the concentration of the target component in the CRDS apparatus in the present embodiment.
Figure 3B:
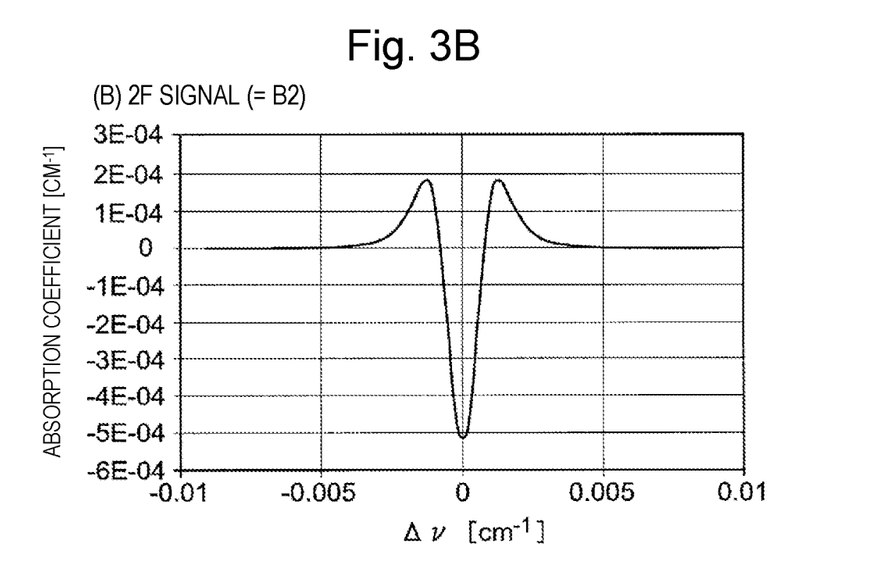
Figure 3C:
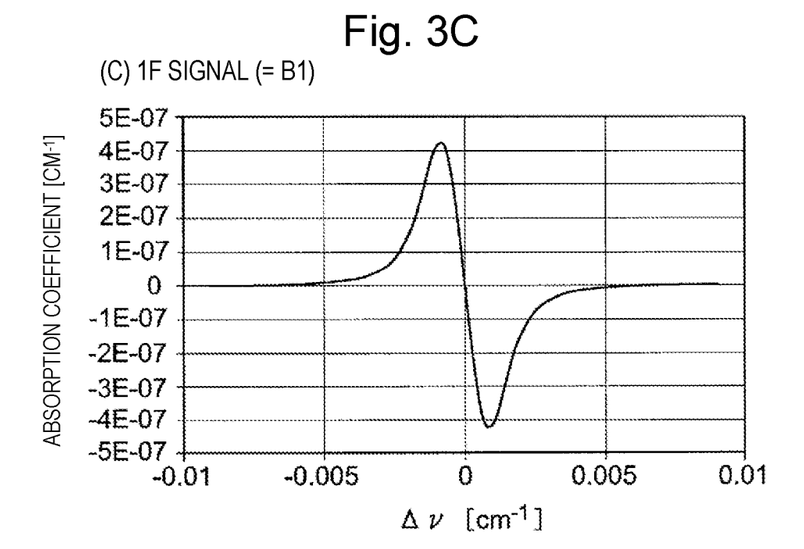
Figure 3D:
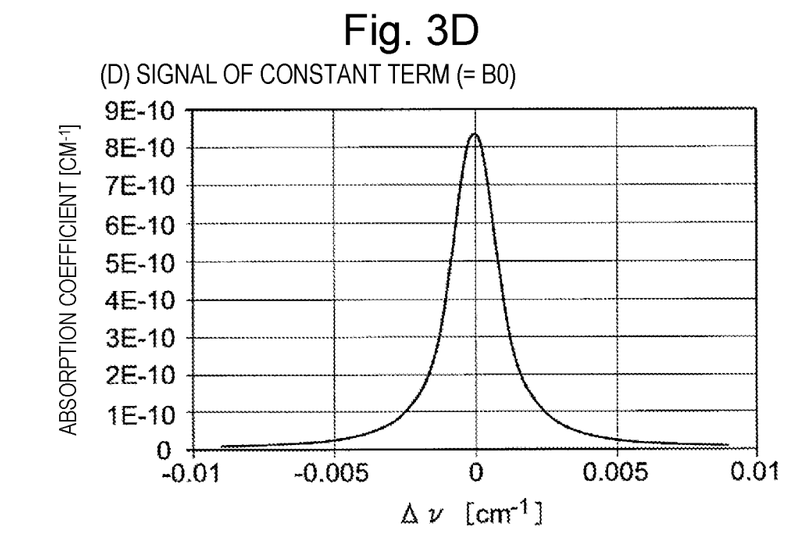

The absorption spectrum is obtained by drawing the CRD signal S(ν) drawn with a wavenumber axis as the horizontal axis. The application of the method disclosed in Patent Literature 1 to this absorption spectrum will be examined. FIGS. 3B, 3C, and 3D illustrate that processing of polynomial approximation disclosed in Patent Literature 1 is applied to an absorption spectrum illustrated in FIG. 3A (here, the horizontal axis is the wavenumber difference Δν axis from the central wavenumber) and obtaining curves corresponding to profiles of the 2f signal (second derivative), the 1f signal (first derivative), and the constant term (0th derivative) of a modulation frequency in laser-wavelength-modulation absorption spectroscopy.

In the method disclosed in Patent Literature 1, polynomial approximation is performed within each range of a wavelength width corresponding to the wavelength modulation width in the absorption spectrum. However, in the method in the present embodiment, it is not necessary to obtain the curve itself as illustrated in FIG. 3B and the like, and it is necessary to obtain only the value of the 2f signal at Δν=0. The reason is as follows.

When S(ν) and α(ν) in the above equation (3) can be approximated by polynomials, S(ν) and α(ν) can be expressed by the following equations, respectively.

$$S(\nu)=b_0'+b_1'(\nu-<\nu>)+b_2'(\nu-<\nu>)^2+b_3'(\nu-<\nu>)^3+ \cdots \quad (4)$$

$$\alpha(\nu)=b_0+b_1(\nu-<\nu>)+b_2(\nu-<\nu>)^2+b_3(\nu-<\nu>)^3+ \cdots \quad (5)$$

Here, <ν> is the wavelength at the center of the wavelength range for acquiring the absorption spectrum, that is, the position of Δν=0 in the present embodiment.

Results of comparing coefficients of terms in the equations (4) and (5) are as follows.

$$b_0' \approx b_0+(R-R')/L \quad (6)$$

$$b_1' \approx b_1 \quad (7)$$

$$b_2' \approx b_2 \quad (8)$$

The equation (8) means that the coefficient $b_2$ of the quadratic term in the polynomial does not depend on the variation of the reflectance of the mirror. Note that, according to the equation (7), the coefficient $b_1$ of the first-order term does not depend on the fluctuation in the reflectance of the mirror in the mathematical formula. However, as is clear from FIG. 3C, the values of the odd-order terms including the first-order term are 0 at the peak top wavelength of the absorption peak of the target component. Therefore, when the absorption intensity by the target component is obtained, it is not possible to use the odd-order terms of the approximate polynomial, and it is possible to use only the coefficients of the even-order terms of the second order or higher.

Further, the method disclosed in Patent Literature 1 targets the absorption spectrum acquired by direct laser absorption spectroscopy. In the direct laser absorption spectroscopy, when the intensity of the laser light cast into the measured gas fluctuates, the fluctuation appears in the absorption spectrum. In order to avoid the fluctuation appearing, a value depending on only the transmission characteristics without depending on the fluctuations in light intensity is obtained by performing normalization processing of dividing the the $b_2$ signal obtained by polynomial approximation by the $b_1$ signal and $b_0$ signal. On the other hand, in the CRDS, in principle, the fluctuations in the light intensity of light incident to the measured gas do not influence the measured value. Therefore, it is possible to use the coefficient itself of the quadratic term obtained by polynomial approximation without performing the normalization processing described above.

In the above description, a case where the reflectance of the mirror differs between the ring-down time $\tau_0$ measurement in the reference state and the ring-down time measurement for the measured gas is assumed. However, as described above, it is possible to use the coefficient of the even-ordered terms of the second order or higher in the approximate polynomial for the absorption spectrum to obtain a signal that is less influenced by the above fluctuation factors, in a similar manner, when the effective optical resonator length changes, or when both the optical resonator length and the reflectance of the mirror change.

When the drift occurs in the resonator length, and the optical resonator length in measurement of the ring-down time $\tau_0$ is set as L and the optical resonator length in measurement of the ring-down time τ is set as L', the CRD signal S(ν) calculated from the measurement result is the following equation (9).

$$S(\nu)=(1/c)\{(1/\tau)-(1/\tau_0)\}=(1/c)\{(c[(1-R)+\alpha(\nu)L']/L')-(c[1-R]/L)\}=\alpha(\nu)+\{(1-R)(L-L')/L \cdot L'\} \quad (9)$$

Further, when the drift occurs in both the reflectance of the mirrors 47 and 48 and the resonator length in the optical resonator 4, the CRD signal S(ν) calculated from the measurement result is the following equation (10).

$$S(\nu)=(1/c)\{(1/\tau)-(1/\tau_0)\}=(1/c)\{(c[(1-R')+\alpha(\nu)L']/L')-(c[1-R]/L)\}=\alpha(\nu)+\{[(1-R')L-(1-R)L']/L \cdot L'\} \quad (10)$$

Since the equations are similar to the equation (3), it is understood that, in this case as well, it means that the coefficient $b_2$ of the quadratic term of the approximate polynomial of S(ν) does not depend on the fluctuations.

Note that, assuming that the drift in the reflectance of the mirror and the optical resonator length has wavelength dependency of the laser light, an error also occurs in the 2f signal calculated from the CRD signal S(v) obtained by the measurement, and the equation (8) may not be established. However, since there is no factor depending on the wavelength of the laser light for the fluctuation in the resonator length, it is possible to ignore the wavelength dependency. Meanwhile, regarding the decrease in the reflectance due to the adhesion of substances in the measured gas to the mirror, the wavelength dependency can be considered, but the wavelength dependency can be considered as being ignored in the wavenumber range of 1 $cm^{-1}$ or less used here. Thus, here, in order to obtain a signal that is less influenced by the above fluctuation factors, the coefficients of even-ordered terms of the second order or higher in the approximate polynomial for the absorption spectrum may be used.

Returning to the flowchart illustrated in FIG. 2, the processing procedure will be described. In the gas measurement apparatus in the present embodiment, the fitting processing unit 73 determines the coefficient of each term in the polynomial to fit the waveform of the absorption peak on the absorption spectrum with a quadratic polynomial (Step S3: processing step). In the fitting processing, for example, known methods such as the least square method can be used. Since the shape in the vicinity of the peak top of the absorption peak may be able to appropriately approximated, a quadratic polynomial may be used as the polynomial, and fitting may be performed only in the wavelength range of about ½ of the peak width of the absorption peak. Thus, for the absorption peak illustrated in FIG. 3A, fitting may be performed for the peak waveform in the range surrounded by the dotted line in FIG. 3A. That is, it is sufficient to perform the measurement in Step S1 only in this wavelength range. Then, the fitting processing unit 73 acquires the coefficient of the quadratic term in the approximate polynomial (Step S4: processing step).

As described above, the coefficient of the quadratic term directly corresponds to the absorption intensity (absorption coefficient). Thus, the relation between the coefficient of the quadratic term and the absorption intensity for the target component (and other components that may be measured) is obtained by preliminary experiments, and the like, and such a relation is stored in the reference information storage unit 75 in a table format, for example. Note that, information stored in the reference information storage unit 75 can be generated by the user himself or herself, but can also be set to be generated by the manufacturer of the present apparatus. Further, since the absorption intensity depends on the temperature and the pressure of the measured gas, the information stored in the reference information storage unit 75 is the relation between the coefficient of the quadratic term and the absorption intensity under a predetermined temperature and predetermined pressure. It is assumed that the measurement of the measured gas is performed under the same predetermined temperature and predetermined pressure.

The concentration calculation unit 74 collates the coefficient of the quadratic term obtained based on the actual measurement with the information stored in the reference information storage unit 75, and acquires the corresponding absorption intensity (Step S5: result obtaining step). Then, the absolute concentration of the target component in the measured gas is calculated from the absorption intensity (Step S6), and the result is output to the output unit 9 and displayed.

As described above, in the gas measurement apparatus in the present embodiment, it is possible to reduce the influence of the drift including short-term fluctuation in the measured value, and to calculate the concentration with high accuracy. Further, in the gas measurement apparatus in the present embodiment, since the measurement may be performed only in a wavelength range that centers on the peak top of the absorption peak and is relatively narrow, it is possible to reduce the measurement time. It is also possible to improve the measurement accuracy by improving the measurement throughput by the amount of reducing the measurement time, or instead by increasing the number of times of repeating the measurement for the same measured gas and integrating the measurement results.

It should be noted that the above embodiment is an example of the present invention, and it is clear that appropriate changes, modifications, additions, and the like of the present invention are included in the claims within the scope of the present invention.

REFERENCE SIGNS LIST

1 . . . Laser-Light Source
2 . . . Laser Driving Unit
3 . . . Optical Switch
4 . . . Optical Resonator
40 . . . Measurement Cell
41 . . . Gas Introduction Tube
42 . . . Introduction Valve
43 . . . Gas Discharge Tube
44 . . . Discharge Valve
47, 48 . . . Mirror
5 . . . Photodetector
6 . . . Measurement Controller
7 . . . Data Processing Unit
71 . . . Ring-Down Time Calculation Unit
72 . . . Spectrum Generator
73 . . . Fitting Processing Unit
74 . . . Concentration Calculation Unit
75 . . . Reference Information Storage Unit
8 . . . Input Unit
9 . . . Output Unit

The invention claimed is:

1. A gas measurement apparatus for obtaining concentration of a target component in a gas to be measured by cavity ring-down absorption spectroscopy, the apparatus comprising
a laser-light source configured to have a variable wavelength;
an optical resonator which includes a pair of highly-reflective mirrors and a measurement cell in which the gas to be measured is to be contained, and resonates laser light which is emitted from the laser-light source and is introduced into the measurement cell;
an optical detection unit configured to detect laser light output from the optical resonator;
a measurement controller configured to control the apparatus so that the laser-light source causes laser light to be incident to the optical resonator, and a wavelength of the laser light is scanned within a predetermined wavelength range, the range including an absorption peak of the target component, thereby performing the cavity ring-down absorption spectroscopy measurement through an output of the optical detection unit;
a spectrum generator configured to generate an absorption spectrum based on data obtained at each wavelength within the predetermined wavelength range under the control of the measurement controller;
a processing unit configured to approximate a waveform shape of the absorption peak of the target component in the absorption spectrum with a polynomial and configured to acquire a coefficient of a term of a predetermined degree in the polynomial; and
a result obtaining unit configured to obtain absorption intensity from the coefficient obtained by the processing unit based on predetermined reference information indicating a correspondence relation between a coefficient of the term of the predetermined degree and the absorption intensity.

2. The gas measurement apparatus according to claim 1, wherein
the polynomial is a quadratic polynomial, and
the term of the predetermined degree is a quadratic term.

3. The gas measurement apparatus according to claim 2, wherein
the measurement controller performs wavelength scanning in a wavelength range necessary and sufficient for calculating a coefficient of the quadratic term of the polynomial.

4. The gas measurement apparatus according to claim 3, wherein
the necessary and sufficient wavelength range is a wavelength range corresponding to about ½ of a peak width of the absorption peak of the target component.

5. A gas measurement method for obtaining concentration of a target component in a gas to be measured by cavity ring-down absorption spectroscopy, the method comprising:
a measurement step of performing the cavity ring-down absorption spectroscopy measurement through optical detection while laser light is incident to an optical resonator and a wavelength of the laser light is scanned within a predetermined wavelength range including an absorption peak of the target component, the optical resonator including a pair of high-reflective mirrors and a measurement cell in which the gas to be measured is contained;
a spectrum generation step of generating an absorption spectrum based on data obtained at each wavelength within the predetermined wavelength range in the measurement step;
a processing step of approximating a waveform shape of the absorption peak of the target component in the absorption spectrum with a polynomial and acquiring a coefficient of a term of a predetermined degree in the polynomial; and
a result obtaining step of obtaining absorption intensity from the coefficient based on predetermined reference information indicating a correspondence relation between a coefficient of the term of the predetermined degree and the absorption intensity.

6. The gas measurement method according to claim 5, wherein
the polynomial is a quadratic polynomial, and
the term of the predetermined degree is a quadratic term.

7. The gas measurement method according to claim 6, wherein
the measurement step performs wavelength scanning in a wavelength range necessary and sufficient for calculating a coefficient of the quadratic term of the polynomial.

8. The gas measurement method according to claim 7, wherein
the necessary and sufficient wavelength range is a wavelength range corresponding to about ½ of a peak width of the absorption peak of the target component.

* * * * *